United States Patent
Sugiyama et al.

(10) Patent No.: US 7,393,519 B2
(45) Date of Patent: Jul. 1, 2008

(54) BASE FOR ORAL COMPOSITION AND THE ORAL COMPOSITION

(75) Inventors: Shinji Sugiyama, Atsugi (JP); Shigeyuki Ejiri, Yokohama (JP); Mitsufumi Matsumoto, Machida (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 11/124,128

(22) Filed: May 9, 2005

(65) Prior Publication Data

US 2005/0207994 A1 Sep. 22, 2005

Related U.S. Application Data

(63) Continuation of application No. PCT/JP03/14196, filed on Nov. 7, 2003.

(30) Foreign Application Priority Data

Nov. 7, 2002 (JP) ............................. 2002-323296

(51) Int. Cl.
  *A61K 8/00* (2006.01)
  *A61Q 11/00* (2006.01)
(52) U.S. Cl. ............................. 424/49; 424/53; 514/835
(58) Field of Classification Search ....................... None
  See application file for complete search history.

(56) References Cited

U.S. PATENT DOCUMENTS

| 4,071,615 A | * | 1/1978 | Barth | 424/52 |
| 4,159,316 A | | 6/1979 | Januszewski et al. | 424/49 |
| 4,584,189 A | * | 4/1986 | Leipold | 424/54 |
| 4,627,972 A | | 12/1986 | Gioffre et al. | 424/49 |
| 5,266,304 A | | 11/1993 | Baffelli et al. | 424/49 |
| 5,631,000 A | | 5/1997 | Pellico et al. | 424/49 |
| 5,718,886 A | | 2/1998 | Pellico | 424/49 |
| 2002/0006422 A1 | | 1/2002 | Koda et al. | 424/49 |

FOREIGN PATENT DOCUMENTS

| EP | 1 123 696 A1 | | 8/2001 |
| EP | 1 566 166 A1 | | 8/2005 |
| JP | 55-100310 | | 7/1980 |
| JP | 2-59513 | | 2/1990 |
| JP | 4-290819 | | 10/1992 |
| JP | 5-117145 | | 5/1993 |
| JP | 8-283133 | | 10/1996 |
| JP | 2001-163745 | | 6/2001 |
| JP | 2002-114656 | * | 4/2002 |
| JP | 2002-114657 | | 4/2002 |
| JP | 2002-255772 | | 9/2002 |
| WO | WO 86/02830 | | 5/1986 |
| WO | WO 94/27565 | | 12/1994 |

OTHER PUBLICATIONS

Machine translation of Japanese Patent Publication 2002-114656 (publication date Apr. 16, 2002).*
Jashawant J. Modi, et al., "Klucel® hydroxypropylcellulose for thickening anhydrous or low-water content (10% or less) systems", Research Disclosure, Mason Publications, vol. 475, No. 113, XP-007133161, Nov. 2003, 1 page.

* cited by examiner

*Primary Examiner*—Frederick Krass
*Assistant Examiner*—Walter E Webb
(74) *Attorney, Agent, or Firm*—Oblon, Spivak, McClelland, Maier & Neustadt, P.C.

(57) ABSTRACT

A non-aqueous toothpaste comprises ascorbic acid or a salt thereof, mixed in a base which is a combination of hydroxypropyl cellulose and 1,3-butylene glycol which is thereby essentially water-free thereby stabilizing the ascorbic acid or a salt thereof.

6 Claims, No Drawings

BASE FOR ORAL COMPOSITION AND THE ORAL COMPOSITION

This application is a continuation of PCT/JP03/14196, filed Nov. 7, 2003.

TECHNICAL FIELD

The present invention relates to a base for oral compositions. In particular, the present invention relates to a base for oral compositions suitable for the use for preparing water-free or substantially water-free oral compositions. The present invention also relates to an oral composition containing the base for the oral composition.

BACKGROUND ART

Oral compositions such as dentifrices generally contain a binding agent such as sodium carboxymethyl cellulose, carrageenan or xantham gum. When such a component is dissolved in water, it becomes viscous and binds a powder component such as an abrasive with a liquid component to realize a shape retention or a suitable viscosity.

Therefore, in water-free oral compositions such as dentifrices, it is difficult to keep the shape retention because of the lack in the viscosity and, as a result, a powdery component is separated from a liquid component in the oral composition with time.

On the other hand, various active ingredients are sometimes contained in the oral compositions such as dentifrices for the purpose of imparting some functions or effects to them. The active ingredients include components for accelerating remineralization (recrystalization), fluorides, sterilizers, anti-inflammatory agents, hemostatics and various enzymes.

The components for accelerating remineralization (recrystalization) include calcium phosphate compounds such as hydroxyapatite. In these compounds, α-tricalcium phosphate (hereinafter referred to as "α-TCP") is known to exhibit an extremely high effect of accelerating remineralization (recrystalization) in the oral cavity and also to be effective in preventing and repairing tooth decay. However, on the other hand, α-TCP is converted to an apatite compound in the presence of water. This reaction is accelerated in the presence of a fluoride or a water-soluble calcium phosphate to cause a self-curing reaction. Thus, α-TCP could not be stably contained in oral compositions such as ordinary water-containing dentifrices.

The fluorides include sodium fluoride, potassium fluoride, sodium monofluorophosphate, tin fluorides, etc. The effect of the fluorides is that hydroxyapatite of teeth is fluorinated with fluorine ion to improve the quality of the teeth. When a fluoride is contained into an ordinary water-containing oral composition such as a dentifrice, fluorine ion is dissolved in water in the oral composition and then adsorbed on other components such as an abrasive not to develop the exhibition of the essential effect of fluorine ion. For example, it is known that in a water-containing oral composition which also contains a sodium fluoride or a tin fluoride and an abrasive such as calcium phosphate or calcium carbonate, fluorine ion adsorbs on the abrasive to inactivate fluorine ion.

The enzymes include, for example, lysozyme, mutanase, protease, amylase and dextranase. Many of these enzymes have a problem that when such an enzyme is contained into a water-containing composition, it causes the hydrolysis to lower the enzymatic activity. Therefore, when such an enzyme is to be contained into such a water-containing composition, a difficultly decomposable enzyme must be selected or a method for stably incorporating each enzyme must be selected.

Hinokitiol as a natural sterilizer or ε-aminocaproic acid as a hemostatic is contained into an oral composition such as a dentifrice in some cases. However, when such an active ingredient is contained into a water-containing composition, the quantitative values thereof are inclined to be lowered by the hydrolysis. Further, it is known that ascorbic acid and salts thereof are effective on the hemorrhage in cases of gingivitis and periodontitis, etc. However, the decomposition reaction thereof easily proceeds in the presence of water to lower the content of ascorbic acid or a salt thereof and also to cause coloring of the composition.

All the problems of the stability of these active ingredients are caused by water contained in the oral compositions such as dentifrices. Under these conditions, it is demanded to develop a substantially water-free oral composition such as a dentifrice which can stably contain α-TCP, fluorides, enzymes, hinokitiol, ε-aminocaproic acid, ascorbic acid, etc. and which can have a shape-retaining property and wherein the separation of the powdery component from the liquid component with time does not occur.

As bases for the oral composition, which are suitable for substantially water-free or non-aqueous oral composition, for example, bases containing agar or gelatin were proposed in Japanese Patent Unexamined Publication No. 2002-114656; bases containing polyethylene powder or polyethylene wax were proposed in Japanese Patent Unexamined Publication No. 2002-114657; and bases containing polyvinylpyrrolidone were proposed in Japanese Patent Unexamined Publication No. 2002-255772.

DISCLOSURE OF THE INVENTION

An object of the present invention is to provide a base for oral compositions suitable for the preparation of water-free or substantially water-free oral compositions. Another object of the present invention is to provide a base for oral compositions suitable for the preparation of water-free or substantially water-free oral compositions excellent in the shape-retaining property which compositions are free from the separation of the components and stable with time. Still another object of the present invention is to provide a base for an oral composition capable of stably containing active ingredients which are generally unstable in the presence of water. A further object of the present invention is to provide an oral composition stably containing active ingredients which are generally unstable in the presence of water, in particular, a water-free or substantially water-free oral composition.

After intensive investigations made for the purpose of attaining the above-described objects, the inventors have found that a highly stable oral composition can be provided by using a base for oral compositions comprising specified components. The present invention has been completed on the basis of this finding.

Namely, the present invention relates to a base for non-aqueous oral compositions, which contains hydroxypropyl cellulose and at least one component selected from the group consisting of concentrated glycerol, diglycerol, propylene glycol, 1,3-butylene glycol and polyethylene glycols. In a preferred embodiment, the present invention also provides the base for non-aqueous oral compositions, which further contains at least one component selected from the group consisting of silicic acid anhydride and crystalline cellulose.

The present invention also relates to an oral composition containing the above-described base for oral composition. In an embodiment of the present invention, the oral composition is preferably a non-aqueous oral composition.

The term "non-aqueous oral composition" herein indicates an oral composition having a water content of 0 to 3% by weight, preferably 0 to 1% by weight and more preferably 0% (completely free of water), based on the whole composition. A base suitable for the preparation of such a non-aqueous oral composition is herein represented as "base for non-aqueous oral composition".

The present invention also relates to an oral composition containing the above-described base for the oral composition and an active ingredient unstable in the presence of water. The active ingredients unstable in the presence of water include, for example, α-tricalcium phosphate (α-TCP), fluorides, enzymes, hinokitiol, ε-aminocaproic acid, ascorbic acid and ascorbic acid salts.

Concretely, the oral composition of the present invention contains the above-described base for the oral composition and at least one of the above-described active ingredients unstable in the presence of water.

Concretely, the oral composition of the present invention comprises the above-described base for the oral composition and at least one active ingredient unstable in the presence of water, which is selected from the group consisting of α-tricalcium phosphate (α-TCP), fluorides, enzymes, hinokitiol, ε-aminocaproic acid, ascorbic acid and ascorbic acid salts.

An embodiment of the present invention is an oral composition containing the above-described base for the oral composition and α-tricalcium phosphate (α-TCP). Another embodiment of the present invention is an oral composition containing the above-described base for the oral composition and at least one fluoride. Still another embodiment of the present invention is an oral composition containing the above-described base for the oral composition and at least one of the enzymes. A further embodiment of the present invention is an oral composition containing the above-described base for the oral composition and hinokitiol. Another embodiment of the present invention is an oral composition containing the above-described base for the oral composition and ε-aminocaproic acid. Another embodiment of the present invention is an oral composition containing the above-described base for the oral composition and at least one component selected from the group consisting of ascorbic acid and salts thereof.

A preferred embodiment of the oral composition of the present invention is an oral composition comprising a combination of the above-described base for the oral composition with α-TCP and a fluoride.

THE BEST EMBODIMENT FOR CARRYING OUT THE INVENTION

The term "oral composition" herein indicates dentifrices such as toothpastes, liquid (gel) dentifrices and moist dentifrices, creams, ointments, pastes, mouth refrigerants, mouthwashes, chewing gums and gargles. The oral composition of the present invention is desirably a non-aqueous oral composition.

The hydroxypropyl cellulose contained in the base for the oral composition of the present invention is a nonionic cellulose derivative obtained by reacting cellulose with propylene oxide. The hydroxypropyl cellulose has various viscosities depending on the degree of polymerization of the molecule thereof. The viscosity of the hydroxypropyl cellulose having a low viscosity is about 1 to 4 mPa/S and that having a high viscosity is as high as about 1000 to 5000 mPa/S. For the determination of the viscosity (mPa/S), 2% aqueous hydroxypropyl cellulose solution is used as the sample and also a rotational viscometer is used.

In the present invention, hydroxypropyl cellulose having a viscosity ranging from a low viscosity to a high viscosity can be used. Namely, hydroxypropyl cellulose can be selected from those having a viscosity of 1 to 5000 mPa/S. Two or more kinds of hydroxypropyl cellulose having different viscosities can also be used. In the present invention, hydroxypropyl cellulose having a viscosity in the range of 150 to 4000 mPa/S is preferably used.

Such a hydroxypropyl cellulose is widely used for the preparation of medicines, cosmetics, vinyl polymers, ceramics for parts of electric appliances and sintering agents in fluorescent lamp tubes. In the present invention, hydroxypropyl cellulose thus available on the market is usable.

The amount of one or more kinds of hydroxypropyl cellulose having different viscosities in the oral composition is 0.1 to 15% by weight, preferably 0.5 to 10% by weight, based on the whole oral composition. In view of the intended effects of the present invention and the usefulness of the oral composition, the suitable amount of hydroxypropyl cellulose is in the above-described range.

The base for the oral composition of the present invention further contains at least one component selected from the group consisting of concentrated glycerol, diglycerol, propylene glycol, 1,3-butylene glycol and polyethylene glycol. Among them, propylene glycol and 1,3-butylene glycol are particularly preferred.

Concentrated glycerol, diglycerol, propylene glycol, 1,3-butylene glycol and polyethylene glycol are widely and generally used for the preparation of medicines, cosmetics, foods and miscellaneous goods as well as in petrochemical industry and dye industry. In the present invention, those available on the market are usable.

The amount of at least one of concentrated glycerol, diglycerol, propylene glycol, 1,3-butylene glycol and polyethylene glycol is 10 to 85% by weight, preferably 20 to 60% by weight, based on the whole oral composition. For obtaining the preferred usefulness of the oral composition, the amount of such a component must be in this range.

The base for the oral composition of the present invention can further contain silicic acid anhydride and/or crystalline cellulose.

Silicic acid anhydride is silicon dioxide in the form of a white powder. Silicic acid anhydride can be synthesized by treating sodium silicate with an acid to precipitate silicon dioxide, gelling and aging silicon dioxide and drying and then pulverizing the obtained product. Silicic acid anhydride having a weight loss on drying of not larger than 13% and an ignition loss of not larger than 18% is preferred. The term "weight loss on drying" herein indicates the amount (% by weight) of the components evaporated after heating 1 g of silicic acid anhydride at 105° C. for 2 hours, and the term "ignition loss" herein indicates the amount (% by weight) of the components evaporated after heating 1 g of silicic acid anhydride at 850° C. for 30 minutes.

Such silicic acid anhydride is widely and generally used for the preparation of foods and cosmetics, as well as medicines, agricultural and horticultural preparations, foods for living things, in ink industry, rubber industry and plastic industry.

Silicic acid anhydride content of the oral composition is 0.5 to 30% by weight, preferably 3 to 15% by weight, based on the whole oral composition. In view of the intended effects of the present invention and the usefulness of the oral composition, the suitable amount of silicic acid anhydride is in the above-described range.

The term "crystalline cellulose" indicates a cellulose crystallite polymer having a substantially constant degree of polymerization, which is obtained by hydrolyzing α-cellulose, obtained in the form of a pulp from a fibrous plant, with an acid or an alkali.

The crystalline cellulose is widely and generally used for the preparation of foods and cosmetics as well as medicines, agricultural and horticultural preparations and foods for living things.

Crystalline cellulose content of the oral composition of the present invention is 0.5 to 30% by weight, preferably 3 to 10% by weight, based on the whole oral composition. In view of the intended effects of the present invention and the usefulness of the oral composition, the suitable amount of the crystalline cellulose is in the above-described range.

In the present invention, the above-described base for the oral composition can be combined with various components such as additives and active ingredients generally used for the oral composition.

The base for the oral composition of the present invention can be advantageously combined with an active ingredient which is generally unstable in the presence of water. Such active ingredients include, for example, α-TCP, fluorides, enzymes, hinokitiol, ε-aminocaproic acid, ascorbic acid and ascorbic acid salts.

The term "α-TCP" used for the preparation of the oral composition of the present invention is α-tricalcium phosphate ($3Ca_3(PO_4)_2 \cdot Ca(OH)_2$) which is widely and generally used for the preparation of medicines, cosmetics, foods and miscellaneous goods as well as in petrochemical industry. In the present invention, α-TCP available on the market is usable.

α-TCP content of the oral composition of the present invention is 0.1 to 50% by weight, preferably 1 to 30% by weight, based on the whole oral composition. For exhibiting the remineralization (recrystalization) effect of α-TCP, α-TCP content must be at least 0.1% by weight. On the other hand, when α-TCP content is over 50% by weight, the usability of the oral composition might be damaged.

When α-TCP is used in combination with a fluoride, an extremely excellent effect is exhibited because of the combination of the remineralization (recrystalization) effect with the supply of fluorine ion. Therefore, the combination of α-TCP with a fluoride which will be described below is preferably used.

Concretely, the fluorides used in the present invention include sodium fluoride, potassium fluoride, sodium monofluorophosphate, tin fluorides, etc. At least one of these fluorides can be used. These fluorides are generally widely used for the preparation of medicines, cosmetics, etc. In the present invention, those available on the market can be used.

The fluoride content of the oral composition of the present invention is 0.01 to 3% by weight based on the whole oral composition, and it is preferably 100 to 1000 ppm in terms of fluorine in the oral composition such as a dentifrice.

Preferred fluorides are sodium fluoride and sodium monofluorophosphate.

Examples of the enzymes usable for the oral composition of the present invention include lysozyme, mutanase, protease, amylase, dextranase and the like. One or more of these enzymes can be used. These enzymes are generally widely used for the preparation of medicines, cosmetics, foods, etc. In the present invention, those available on the market can be used.

The enzyme content of the oral composition of the present invention is 0.01 to 5% by weight, preferably 0.1 to 2% by weight, based on the whole oral composition.

Preferred enzymes are lysozyme and amylase.

Hinokitiol used for the preparation of the oral composition of the present invention is a crystalline acidic compound which is a specific component contained in natural *Aomori hinoki* trees. Other kinds of trees containing hinokitiol are, for example, Taiwanese *hinoki* trees and Western red cedar trees in North America. Hinokitiol having a strong antibacterial activity and a wide antimicrobial spectrum is one of few natural sterilizers.

Hinokitiol as described above is generally widely used for the preparation of foods, cosmetics, medicines, agricultural and horticultural preparations, construction materials, foods for living things, etc. In the present invention, those available on the market can be used.

Hinokitiol content of the oral composition of the present invention is 0.005 to 0.5% by weight, preferably 0.01 to 0.2% by weight, based on the whole oral composition.

ε-Aminocaproic acid used for the preparation of the oral composition of the present invention is a component having anti-plasmin effect, hemostatic effect and anti-inflammatory effect and generally widely used for the preparation of cosmetics, medicines, foods and agricultural and horticultural preparations. In the present invention, ε-aminocaproic acid available on the market can be used.

ε-Aminocaproic acid content of the oral composition of the present invention is 0.001 to 1% by weight, preferably 0.006 to 0.2% by weight, based on the whole oral composition.

Ascorbic acid used for the preparation of the oral composition of the present invention is so-called vitamin C. Concretely, ascorbic acid herein indicates L-ascorbic acid ($C_6H_8O_6=176$) and salts thereof. Concretely, the ascorbic acid salts used herein include sodium ascorbate, potassium ascorbate, calcium ascorbate, magnesium ascorbate, etc. The oral composition of the present invention can contain one or more components selected from the group consisting of ascorbic acid and salts thereof. In the ascorbic acid salts, sodium ascorbate is preferably used.

Ascorbic acid and the salts thereof are components having anti-inflammatory effect and also effect of accelerating the synthesis of collagen fibers. They are generally widely used for the preparation of cosmetics, medicines, foods, and agricultural and horticultural preparations. In the present invention, those available on the market can be used.

The amount of at least one component selected from the group consisting of ascorbic acid and salts thereof in the oral composition of the present invention is 0.001 to 20% by weight, preferably 0.01 to 10% by weight, based on the whole oral composition.

As described above, the active ingredients which can be suitably used in combination with the base for the oral composition of the present invention are (1) α-TCP; (2) fluorides; (3) enzymes; (4) hinokitiol; (5) ε-aminocaproic acid; and (6) ascorbic acid and salts thereof. One or more compounds selected from the group consisting of these components (1) to (6) can be contained into the oral composition. Two or more compounds can be selected from two or more of these groups and used together. In particular, the combination of α-TCP with the fluoride is preferred.

The oral composition of the present invention can contain, if necessary, components which will be described below in an ordinary amount, in addition to the above-described components, depending on the kind of the composition.

<Abrasives>

The abrasives include silica abrasives such as silica gel, precipitated silica, igneous silica, hydrated silicic acid, zeolite, aluminosilicate and zirconosilicate; as well as dicalcium phosphate dihydrate, anhydrous dicalcium phosphate, calcium pyrophosphate, magnesium tertiary phosphate, tricalcium phosphate, aluminum hydroxide, alumina, light calcium carbonate, heavy calcium carbonate, magnesium carbonate, zirconium silicate and synthetic resin abrasives. They can be used either alone or in combination of two or more of them. The amount of the abrasive is preferably 3 to 60% by weight, more preferably 10 to 45% by weight, based on the whole composition.

<Humectants>

One or more of polyhydric alcohols such as sorbitol and maltitol are usable.

<Foaming Agents>

The foaming agents include, for example, sodium lauryl sulfate, sodium lauroyl sarcosine, sodium alkyl sulfosuccinates, sodium coconut oil fatty acid monoglycerol sulfonates, sodium α-olefin sulfonates, N-acylamino acid salts such as N-acyl glutamate, 2-alkyl-N-carboxymethyl-N-hydroxyethylimidazolinium betaine, maltitol fatty acid esters, sucrose fatty acid esters, polyglycerol fatty acid esters, fatty acid diethanolamides, polyoxyethylene sorbitan monostearate, polyoxyethylene hydrogenated castor oil and polyoxyethylene fatty acid esters. These foaming agents are usable either alone or in combination of two or more of them.

<Sweeteners>

The sweeteners include, for example, saccharin sodium, aspartame, trehalose, stevioside, stevia extract, p-methoxycinnamic aldehyde, neohesperidyldihydrochalcone and perillartine. These sweetening agents are usable either alone or in combination of two or more of them.

<Antiseptics>

The antiseptics include, for example, p-hydroxybenzoate esters such as methylparaben, ethylparaben, propylparaben and butylparaben, sodium benzoate, phenoxyethanol and alkyldiaminoethylglycine hydrochlorides. These antiseptics are usable either alone or in combination of two or more of them.

<Flavoring Components>

The flavoring components include, for example, 1-menthol, anethole, menthone, cineole, limonene, carvone, methyl salicylate, ethyl butyrate, eugenol, thymol, cinnamic aldehyde and trans-2-hexenal. These flavoring components are usable either alone or in combination of two or more of them. They can be used as they are or in the form of an essential oil containing them.

The above-described flavoring components may be used in combination with other flavoring components such as aliphatic alcohols and esters thereof, terpene hydrocarbons, phenol ethers, aldehydes, ketones and lactones as well as essential oils so far as the effect of the present invention is not disturbed. The amount of the flavors is preferably 0.02 to 2% by weight based on the whole composition.

<Active Ingredients>

The active ingredients include, for example, zeolite, chlorhexidine salts, cetylpyridinium chloride, benzalkonium chloride, benzethonium chloride, bisabolol, triclosan, isopropylmethylphenol, tocopherol acetate, tranexamic acid, dihydrocholesterol, polyvinylpyrrolidone, glycyrrhetinic acid, glycyrrhizinic acid salts, copper chlorophyllin salts, sodium chloride and guaiazulene sulfonate. They are usable either alone or in combination of two or more of them.

<Others>

Other components usable herein are, for example, coloring matters such as Blue No. 1, pigments such as titanium oxide, antioxidants such as dibutylhydroxytoluene, and corrigents such as a liquid extracted from cha by dry distillation and sodium glutamate.

When 3% by weight or less of water is contained into the oral composition of the present invention, binding agents as described below can be contained, if necessary, into the composition comprising the above-described components.

<Binding Agents>

The binding agents include, for example, carrageenan (ι, λ, κ), alginic acid, alginic acid salts and derivatives thereof such as sodium alginate, alginic acid propylene glycol ester, calcium-containing sodium alginate, potassium alginate, calcium alginate and ammonium alginate, xantham gum, guar gum, gelatin, agar, sodium carboxymethyl cellulose, hydroxyethyl cellulose and polysodium acrylates. They are usable either alone or in combination of two or more of them.

The oral composition comprising the combination of the above-described components can be prepared by an ordinary method which is not particularly limited.

The composition such as a tooth paste obtained as described above can be stuffed into aluminum tubes, laminate tubes, glass vapor-deposited tubes, plastic tubes, plastic bottles, aerosol vessels, etc.

EXAMPLES

The following Examples and Comparative Examples will further illustrate the present invention, which by no means limit the invention. Various tooth pastes each having a composition shown in Tables 1 to 4 (unit: weight %) were prepared by an ordinary method and then tested as will be described below. The test results are summarized in Tables 1 to 4.

1. Tooth Paste Storability Tests

Tooth pastes shown in Table 1 were prepared and then stored under severe conditions as shown below. After the storage under severe conditions, the conditions of the respective tooth pastes were organoleptically evaluated according to the following evaluation standards:

[Severe Storage Conditions]
1. Storage in a constant temperature bath at 60° C. for one month
2. Storage in a constant temperature bath at 50° C. for two months.

[Evaluation Standard]
○: The state of the tooth paste was the same as that immediately after the preparation.
X: The separation of the solid component from the liquid component was confirmed.

TABLE 1

|  | Example | | Comparative Example | | | |
| --- | --- | --- | --- | --- | --- | --- |
| Component (%) | 1 | 2 | 1 | 2 | 3 | 4 |
| Hydroxypropylcellulose (Viscosity 150-400 mPa/S) | 2.0 | 2.0 | — | — | — | — |
| 1,3-Butylene glycol | 61.8 | 49.8 | 63.8 | 51.8 | 48.8 | 48.8 |
| Silicic acid anhydride | — | 12.0 | — | 12.0 | 12.0 | 12.0 |
| Carrageenan | — | — | — | — | 3.0 | — |
| Sodium carboxymethylcellulose | — | — | — | — | — | 3.0 |

TABLE 1-continued

|  | Example | | Comparative Example | | | |
|---|---|---|---|---|---|---|
| Component (%) | 1 | 2 | 1 | 2 | 3 | 4 |
| Aluminum hydroxide | 35.0 | 35.0 | 35.0 | 35.0 | 35.0 | 35.0 |
| Sodium lauryl sulfate | 1.0 | 1.0 | 1.0 | 1.0 | 1.0 | 1.0 |
| Saccharin sodium | 0.1 | 0.1 | 0.1 | 0.1 | 0.1 | 0.1 |
| Ethylparaben | 0.1 | 0.1 | 0.1 | 0.1 | 0.1 | 0.1 |
| Total | 100.0 | 100.0 | 100.0 | 100.0 | 100.0 | 100.0 |
| State stability after storage at 60° C. for 1 month | ○ | ○ | X | X | X | X |
| State stability after storage at 50° C. for 2 months | ○ | ○ | X | X | X | X |

2. Fluorine Ion Determination Test

Tooth pastes shown in Table 2 were prepared and stored under severe conditions shown below. After the storage under severe conditions, a predetermined amount of the tooth paste was taken and dispersed in water. The obtained aqueous dispersion was immediately centrifuged to separate the dispersion into an aqueous layer and a solid layer. Fluorine ion concentration in the liquid layer was determined with a fluorine ion meter. Fluorine ion detected in this sample was considered to be active fluorine ion which was not adsorbed on other components in the tooth paste. The residual rate of active fluorine ion was determined according to formula (1) given below.

[Severe Storage Conditions]
1. Storage in a constant temperature bath at 60° C. for one week
2. Storage in a constant temperature bath at 60° C. for two weeks.

Residual rate (%)=[(Amount of fluorine ion after the storage under severe conditions)/(Amount of fluorine ion immediately after the preparation of tooth paste). [Formula (1)]

When fluorine ion residual rate, i.e. active fluorine ion content, of the tooth paste stored under the severe conditions was 80% or higher, the fluoride was judged to be stable.

The storability tests of the tooth pastes shown in Table 2 were carried out in the same manner as that in above item 1.

TABLE 2

|  |  | Example | | Comp. Ex. | | Ref. |
|---|---|---|---|---|---|---|
| Components (%) | | 3 | 4 | 5 | 6 | Ex. 1 |
| Hydroxypropylcellulose (Viscosity 150-400 mPa/S) | | 3.0 | 3.0 | — | — | 3.0 |
| 1,3-Butylene glycol | | 60.6 | 48.6 | — | 48.6 | 18.6 |
| Silicic acid anhydride | | — | 12.0 | 12.0 | 12.0 | 12.0 |
| Carrageenan | | — | — | 2.0 | 3.0 | — |
| Water | | — | — | 49.6 | — | 30.0 |
| Sodium fluoride | | 0.2 | 0.2 | 0.2 | 0.2 | 0.2 |
| Calcium hydrogenphosphate | | 35.0 | 35.0 | 35.0 | 35.0 | 35.0 |
| Sodium lauryl sulfate | | 1.0 | 1.0 | 1.0 | 1.0 | 1.0 |
| Saccharin sodium | | 0.1 | 0.1 | 0.1 | 0.1 | 0.1 |
| Ethylparaben | | 0.1 | 0.1 | 0.1 | 0.1 | 0.1 |
| Total | | 100.0 | 100.0 | 100.0 | 100.0 | 100.0 |
| State stability after storage at 60° C. for 1 month | | ○ | ○ | ○ | X | ○ |
| State stability after storage at 50° C. for 2 months | | ○ | ○ | ○ | X | ○ |
| Fluorine ion residue (%) | Storage at 60° C. for 1 week | 95 | 94 | 45 | 94 | 41 |
|  | Storage at 60° C. for 2 weeks | 92 | 90 | 35 | 91 | 39 |

3. Quantitative Test of ε-Aminocaproic Acid

Tooth pastes shown in Table 3 were prepared and stored under severe conditions shown below. After the storage under severe conditions, the quantity of ε-aminocaproic acid in each tooth paste was determined by the liquid chromatography under the following conditions.

[Severe Storage Conditions]
1. Storage in a constant temperature bath at 60° C. for one month
2. Storage in a constant temperature bath at 50° C. for two months.

[Test Conditions]
Detector: Fluorescent detector (excitation wave length: 390 nm, fluoresce wave length: 480 nm)
Column: Octadecylsilylated silica gel for high-performance liquid chromatography (5 to 10 μm) was fed into a stainless steel tube having an inner diameter of 4.6 mm and a length of 250 mm.
Column temperature: 40° C.
Mobile phase: Phosphoric acid solution/acetonitrile mixture
Flow rate: 1.0 ml/min The residual rate of ε-aminocaproic acid was determined according to the following formula (2):

Residual rate (%)=[(Amount of ε-aminocaproic acid after the storage under severe conditions)/(Amount of ε-aminocaproic acid immediately after the preparation of tooth paste). [Formula (2)]

When ε-aminocaproic acid residual rate in the tooth paste stored under the severe conditions was 90% or higher, ε-aminocaproic acid was judged to be stable.

The storability tests of the tooth pastes shown in Table 3 were carried out in the same manner as that in above item 1.

TABLE 3

|  |  | Example | | Comp. Ex. | | Ref. |
|---|---|---|---|---|---|---|
| Component (%) | | 5 | 6 | 7 | 8 | Ex. 2 |
| Hydroxypropylcellulose (Viscosity 150-400 mPa/S) | | 3.0 | 3.0 | — | — | 3.0 |
| 1,3-Butylene glycol | | 56.7 | 44.7 | 15.7 | 44.7 | 14.7 |
| Silicic acid anhydride | | — | 12.0 | 12.0 | 12.0 | 12.0 |
| Carrageenan | | — | — | 2.0 | 3.0 | — |
| Water | | — | — | 30.0 | — | 30.0 |
| ε-Aminocaproic acid | | 0.1 | 0.1 | 0.1 | 0.1 | 0.1 |
| Aluminum hydroxide | | 35.0 | 35.0 | 35.0 | 35.0 | 35.0 |
| Polyoxyethylene hydrogenated castor oil | | 5.0 | 5.0 | 5.0 | 5.0 | 5.0 |
| Saccharin sodium | | 0.1 | 0.1 | 0.1 | 0.1 | 0.1 |
| Ethylparaben | | 0.1 | 0.1 | 0.1 | 0.1 | 0.1 |
| Total | | 100.0 | 100.0 | 100.0 | 100.0 | 100.0 |
| State stability after storage at 60° C. for 1 month | | ○ | ○ | ○ | X | ○ |
| State stability after storage at 50° C. for 2 months | | ○ | ○ | ○ | X | ○ |
| Residual rate of ε-aminocaproic acid (%) | Storage at 60° C. for 1 month | 100 | 100 | 82 | 99 | 81 |
|  | Storage at 50° C. for 2 months | 100 | 100 | 82 | 99 | 82 |

4. Quantitative Test of Sodium Ascorbate

Tooth pastes shown in Table 4 were prepared and stored under severe conditions shown below. After the storage under severe conditions, the quantity of sodium ascorbate in each tooth paste was determined by the liquid chromatography under the following conditions.

[Severe Storage Conditions]

1. Storage in a constant temperature bath at 60° C. for one month
2. Storage in a constant temperature bath at 50° C. for two months.

[Test Conditions]

Detector: Ultraviolet absorption spectrophotometer (determination wave length: 245 nm)

Column: 5 μm of octadecylsilylated silica gel for high-performance liquid chromatography was fed into a stainless steel tube having an inner diameter of 4.6 mm and a length of 250 mm.

Column temperature: 40° C.

Mobile phase: Metaphosphoric acid solution

Flow rate: 1.0 ml/min

The residual rate of sodium ascorbate was determined according to the following formula (3):

$$\text{Residual rate (\%)} = \frac{\text{(Amount of sodium ascorbate after the storage under severe conditions)}}{\text{(Amount of sodium ascorbate immediately after the preparation of tooth paste)}} \times 100. \quad \text{[Formula (3)]}$$

When sodium ascorbate residual rate of the tooth paste stored under the severe conditions was 90% or higher, sodium ascorbate was judged to be stable.

The storability tests of the tooth pastes shown in Table 4 were carried out in the same manner as that in above item 1.

TABLE 4

| Component (%) | Example 7 | Example 8 | Comp. Ex. 9 | Comp. Ex. 10 | Ref. Ex. 3 |
|---|---|---|---|---|---|
| Hydroxypropylcellulose (Viscosity 150-400 mPa/S) | 3.0 | 3.0 | — | — | 3.0 |
| 1,3-Butylene glycol | 58.9 | 46.9 | 17.9 | 46.9 | 16.9 |
| Silicic acid anhydride | — | 12.0 | 12.0 | 12.0 | 12.0 |
| Carrageenan | — | — | 2.0 | 3.0 | — |
| Water | — | — | 30.0 | — | 30.0 |
| Sodium ascorbate | 1.0 | 1.0 | 1.0 | 1.0 | 1.0 |
| Aluminum hydroxide | 35.0 | 35.0 | 35.0 | 35.0 | 35.0 |
| Sodium lauryl sulfate | 1.0 | 1.0 | 1.0 | 1.0 | 1.0 |
| Saccharin sodium | 1.0 | 1.0 | 1.0 | 1.0 | 1.0 |
| Ethylparaben | 0.1 | 0.1 | 0.1 | 0.1 | 0.1 |
| Total | 100.0 | 100.0 | 100.0 | 100.0 | 100.0 |
| State stability after storage at 60° C. for 1 month | ○ | ○ | ○ | X | ○ |
| State stability after storage at 50° C. for 2 months | ○ | ○ | ○ | X | ○ |
| Residual rate of sodium ascorbate (%) Storage at 60° C. for 1 month | 93 | 94 | 35 | 93 | 38 |
| Residual rate of sodium ascorbate (%) Storage at 50° C. for 2 months | 97 | 96 | 38 | 96 | 37 |

The following facts will be understood from the above-described results of the experiments: It is understood from the results shown in Table 1 that by using the base for the oral composition of the present invention, the obtained tooth paste has the separation-free state and excellent storability. It is understood from the results shown in Tables 2 to 4 that the tooth pastes each comprising the oral composition of the present invention has an excellent stability and also a high storability of the fluoride, ε-aminocaproic acid, ascorbic acid and salts thereof.

The results of the experiments of tooth pastes in Examples 9 to 22 prepared by an ordinary method were similar to those described above.

Example 9

Preparation of a Dental Paste

| | |
|---|---|
| Hydroxypropylcellulose (viscosity 150-400 mPa/S) | 3.0% by weight |
| Polyethylene glycol | 49.65 |
| Crystalline cellulose | 10.0 |
| Aluminum hydroxide | 35.0 |
| Sodium lauryl sulfate | 1.0 |
| Saccharin sodium | 0.1 |
| Paraben | 0.1 |
| Flavor | 1.0 |
| Tocopherol acetate | 0.1 |
| Cetyl pyridinium chloride | 0.05 |
| Total | 100.0% by weight |

Example 10

Preparation of a Dental Paste

| | |
|---|---|
| Hydroxypropylcellulose (viscosity 1000-4000 mPa/S) | 1.0% by weight |
| Diglycerol | 23.0 |
| Propylene glycol | 23.17 |
| Silicic acid anhydride | 5.0 |
| Crystalline cellulose | 10.0 |
| Sodium fluoride | 0.2 |
| Calcium carbonate | 35.0 |
| Sodium lauryl sulfate | 1.0 |
| Sodium lauroyl sarcosine | 0.3 |
| *Stevia* extract | 0.1 |
| Sodium benzoate | 0.1 |
| Flavor | 1.0 |
| Dipotassium glycyrrhizinate | 0.1 |
| Isopropylmethylphenol | 0.03 |
| Total | 100.0% by weight |

Example 11

Preparation of a Dental Paste

| | |
|---|---|
| Hydroxypropylcellulose (viscosity 2-3 mPa/S) | 10.0% by weight |
| Concentrated glycerol | 19.0 |
| Polyethylene glycol | 10.0 |
| 1,3-Butylene glycol | 10.8 |
| Silicic acid anhydride | 10.0 |
| ε-Aminocaproic acid | 0.1 |
| Tin fluoride | 0.1 |
| Calcium hydrogenphosphate for dentifrices | 25.0 |
| Sucrose fatty acid esters | 0.5 |
| Xylitol | 10.0 |
| Carrageenan | 0.3 |
| Paraben | 0.1 |
| Flavor | 1.0 |
| Purified water | 3.0 |
| β-glycyrrhetinic acid | 0.05 |
| Chlorhexidine hydrochloride | 0.05 |
| Total | 100.0% by weight |

Example 12

Preparation of a Dental Paste

| | |
|---|---|
| Hydroxypropylcellulose (viscosity 6-10 mPa/S) | 10.0% by weight |
| Concentrated glycerol | 34.45 |
| Polyethylene glycol | 10.0 |
| Silicic acid anhydride | 10.0 |
| α-TCP | 30.0 |
| Sodium fluoride | 0.2 |

Example 13

Preparation of a Dental Paste

| | |
|---|---|
| Sodium lauryl sulfate | 1.0 |
| Polyoxyethylene hydrogenated castor oil | 3.0 |
| Saccharin sodium | 0.1 |
| Paraben | 0.1 |
| Flavor | 1.0 |
| Tocopherol acetate | 0.1 |
| Glycyrrhizin | 0.05 |
| Total | 100.0% by weight |

Example 13

Preparation of a Dental Paste

| | |
|---|---|
| Hydroxypropylcellulose (viscosity 150-400 mPa/S) | 3.0% by weight |
| Concentrated glycerol | 54.95 |
| Silicic acid anhydride | 20.0 |
| Hydrous silicic acid | 10.0 |
| Crystalline cellulose | 8.0 |
| Chlorinated lysozyme | 0.5 |
| Sodium lauryl sulfate | 1.0 |
| Sodium lauroyl sarcosine | 0.3 |
| *Stevia* extract | 0.1 |
| Paraben | 0.1 |
| Flavor | 1.0 |
| Zeolite | 1.0 |
| Cetylpyridinium chloride | 0.05 |
| Total | 100.0% by weight |

Example 14

Preparation of a Dental Paste

| | |
|---|---|
| Hydroxypropylcellulose (viscosity 6-10 mPa/S) | 5.0% by weight |
| Concentrated glycerol | 23.7 |
| Polyethylene glycol | 20.0 |
| Silicic acid anhydride | 10.0 |
| Hinokitiol | 0.05 |
| ε-Aminocaproic acid | 0.1 |
| Calcium hydrogenphosphate for dentifirices | 15.0 |
| Polyoxyethylene hydrogenated castor oil | 5.0 |
| Trehalose | 5.0 |
| Sorbitol | 5.0 |
| Alkyldiaminoethylglycine hydrochloride solution | 0.05 |
| Flavor | 1.0 |
| Sodium chloride | 10.0 |
| Tocopherol acetate | 0.1 |
| Total | 100.0% by weight |

Example 15

Preparation of a Dental Paste

| | |
|---|---|
| Hydroxypropylcellulose (viscosity 150-400 mPa/S) | 3.0% by weight |
| Polyethylene glycol | 20.0 |
| 1,3-Butylene glycol | 30.25 |
| Silicic acid anhydride | 10.0 |
| Hydrous silicic acid | 20.0 |
| Crystalline cellulose | 10.0 |
| α-TCP | 3.0 |
| Sodium fluoride | 0.2 |
| Sodium lauryl sulfate | 1.0 |
| Sodium lauroyl sarcosine | 0.3 |
| *Stevia* extract | 0.1 |
| Paraben | 0.1 |
| Flavor | 1.0 |
| Zeolite | 1.0 |
| Cetylpyridinium chloride | 0.05 |
| Total | 100.0% by weight |

Example 16

Preparation of a Dental Paste

| | |
|---|---|
| Hydroxypropylcellulose (viscosity 150-400 mPa/S) | 3.0% by weight |
| Polyethylene glycol | 20.0 |
| 1,3-Butylene glycol | 63.25 |
| Silicic acid anhydride | 10.0 |
| Sodium lauryl sulfate | 1.0 |
| Saccharin sodium | 0.5 |
| Paraben | 0.1 |
| Flavor | 1.0 |
| Sodium ascorbate | 1.0 |
| Tocopherol acetate | 0.1 |
| Cetylpyridinium chloride | 0.05 |
| Total | 100.0% by weight |

Example 17

Preparation of a Dental Paste

| | |
|---|---|
| Hydroxypropylcellulose (viscosity 1000-4000 mPa/S) | 1.0% by weight |
| Polyethylene glycol | 20.0 |
| 1,3-Butylene glycol | 46.57 |
| Silicic acid anhydride | 5.0 |
| Calcium hydrogenphosphate for dentifrices | 20.0 |
| Glycerol fatty acid ester | 3.0 |
| *Stevia* extract | 0.1 |
| Sodium benzoate | 1.0 |
| Flavor | 1.0 |
| Sodium ascorbate | 2.0 |
| Sodium fluoride | 0.2 |
| Dipotassium glycyrrhizinate | 0.1 |
| Isopropylmethylphenol | 0.03 |
| Total | 100.0% by weight |

Example 18

Preparation of a Dental Paste

| | |
|---|---|
| Hydroxypropylcellulose (viscosity 150-400 mPa/S) | 1.5% by weight |
| Hydroxypropylcellulose (viscosity 1000-4000 mPa/S) | 0.5% by weight |
| Polyethylene glycol | 10.0 |
| 1,3-Butylene glycol | 37.2 |
| Silicic acid anhydride | 10.0 |
| Calcium hydrogenphosphate for dentifrices | 25.0 |
| Sucrose fatty acid ester | 0.5 |
| Polyoxyethylene hydrogenated castor oil | 3.0 |
| Xylitol | 10.0 |
| Paraben | 0.1 |
| Flavor | 1.0 |
| Purified water | 1.0 |
| Ascorbic acid | 0.1 |
| β-glycyrrhetinic acid | 0.05 |
| Chlorhexidine hydrochloride | 0.05 |
| Total | 100.0% by weight |

Example 19

Preparation of a Dental Paste

| | |
|---|---|
| Hydroxypropylcellulose (viscosity 6-10 mPa/S) | 10.0% by weight |
| Polyethylene glycol | 15.0 |
| 1,3-Butylene glycol | 52.55 |
| Silicic acid anhydride | 10.0 |
| Sodium monofluorophosphate | 0.7 |
| Sodium lauryl sulfate | 1.0 |

-continued

| | |
|---|---|
| Polyoxyethylene hydrogenated castor oil | 3.0 |
| Saccharin sodium | 1.0 |
| Paraben | 0.1 |
| Flavor | 1.0 |
| Ascorbic acid | 0.5 |
| Zeolite | 5.0 |
| Tocopherol acetate | 0.1 |
| Glycyrrhizin | 0.05 |
| Total | 100.0% by weight |

Example 20

Preparation of a Dental Paste

| | |
|---|---|
| Hydroxypropylcellulose (viscosity 150-400 mPa/S) | 3.0% by weight |
| Concentrated glycerol | 30.0 |
| Propylene glycol | 26.65 |
| Silicic acid anhydride | 10.0 |
| Calcium hydrogenphosphate for dentifrices | 20.0 |
| Glycerol fatty acid ester | 1.0 |
| Polyoxyethylene hydrogenated castor oil | 2.0 |
| *Stevia* extract | 0.1 |
| Paraben | 0.1 |
| Flavor | 1.0 |
| Sodium ascorbate | 5.0 |
| Tocopherol acetate | 0.1 |
| Zeolite | 1.0 |
| Cetyl pyridinium chloride | 0.05 |
| Total | 100.0% by weight |

Example 21

Preparation of a Dental Paste

| | |
|---|---|
| Hydroxypropylcellulose (viscosity 150-400 mPa/S) | 2.0% by weight |
| 1,3-Butylene glycol | 49.6 |
| Polyethylene glycol | 10.0 |
| Silicic acid anhydride | 10.0 |
| Calcium carbonate | 20.0 |
| Polyoxyethylene hydrogenated castor oil | 3.0 |
| Saccharin sodium | 1.0 |
| Xylitol | 1.0 |
| Sodium lauryl sulfate | 1.0 |
| Paraben | 0.1 |
| Flavor | 1.0 |
| Sodium ascorbate | 1.0 |
| Cetyl pyridinium chloride | 0.05 |
| β-Glycyrrhetinic acid | 0.05 |
| Sodium fluoride | 0.2 |
| Total | 100.0% by weight |

Example 22

Preparation of a Dental Paste

| | |
|---|---|
| Hydroxypropylcellulose (viscosity 150-400 mPa/S) | 3.0% by weight |
| 1,3-Butylene glycol | 45.1 |
| Polyethylene glycol | 10.0 |
| Silicic acid anhydride | 6.0 |
| Zeolite | 5.0 |
| Calcium hydrogenphosphate for dentifrices | 17.0 |

-continued

| | |
|---|---|
| Anhydrous ethanol | 5.5 |
| Titanium oxide | 3.0 |
| Sodium lauryl sulfate | 1.8 |
| Saccharin sodium | 1.0 |
| Dibutylhydroxytoluene | 0.5 |
| Magnesium phosphate | 0.3 |
| 1-Menthol | 0.3 |
| Peppermint oil | 0.2 |
| Paraben | 0.1 |
| Colorant | 0.1 |
| Sodium ascorbate | 1.0 |
| Tocopherol acetate | 0.1 |
| Total | 100.0% by weight |

INDUSTRIAL APPLICABILITY

By using the base for the oral composition of the present invention, a highly stable, non-aqueous oral composition having a high shape retention can be obtained. It is also possible to obtain a non-aqueous oral composition having excellent shape-retaining property and stability to aging, in which the active ingredients are stably maintained and the solid component is not separated from the liquid component, by combining the base for the oral composition of the present invention with an active ingredient usually unstable in the presence of water, which is selected from the group consisting of α-TCP, fluorides, enzymes, hinokitiol, ε-aminocaproic acid, ascorbic acid and ascorbic acid salts.

What is claimed is:

1. A non-aqueous toothpaste, which comprises:
   ascorbic acid or a salt thereof, mixed in a base which is a combination of hydroxypropyl cellulose and 1,3-butylene glycol in an amount of 10 to 85% by weight based on the weight of the toothpaste.

2. The non-aqueous toothpaste of claim 1, further comprising at least one component selected from the group consisting of silicic acid anhydride and crystalline cellulose.

3. The non-aqueous toothpaste of claim 1, wherein the ascorbic acid or a salt thereof is sodium ascorbate.

4. A non-aqueous toothpaste, which consists of:
   ascorbic acid or a salt thereof, mixed in a base which is a combination of hydroxypropyl cellulose and 1,3-butylene glycol in an amount of 10 to 85% by weight based on the weight of the toothpaste, at least one abrasive, at least one foaming agent, at least one sweetener and at least one antiseptic.

5. The non-aqueous toothpaste of claim 4, wherein the ascorbic acid or a salt thereof is sodium ascorbate.

6. A non-aqueous toothpaste, which consists of:
   ascorbic acid or a salt thereof mixed in a base which is a combination of hydroxypropyl cellulose and 1,3-butylene glycol in an amount of 10 to 85% by weight based on the weight of the toothpaste, silicic acid anhydride, crystalline cellulose, at least one abrasive, at least one foaming agent, at least one sweetener and at least one antiseptic.

* * * * *